United States Patent [19]

Buege et al.

[11] 4,200,691

[45] Apr. 29, 1980

[54] METHOD FOR ISOLATING MB CREATINE KINASE

[75] Inventors: John A. Buege; Michael E. Hickey; Gopal S. Rautela, all of Newark, Del.

[73] Assignee: E. I. Du Pont de Nemours and Company, Wilmington, Del.

[21] Appl. No.: 878,001

[22] Filed: Feb. 15, 1978

[51] Int. Cl.² ............................................. C12Q 1/50
[52] U.S. Cl. ...................................... 435/17; 435/815
[58] Field of Search ............... 195/66 R, 103.5 R, 99; 435/17

[56] References Cited

U.S. PATENT DOCUMENTS 4,049,496  9/1977  Henry ................................. 195/66 R
4,105,499  8/1978  Kiyasu ........................... 195/103.5 R

FOREIGN PATENT DOCUMENTS 1481463  7/1977  United Kingdom .

OTHER PUBLICATIONS

Calmon et al. editors, Ion Exchangers in Organic and Biochemistry, 1957, pp. 380, 492, 630.
Takahashi et al., Clinica Chimica Acta, vol. 38, pp. 285–290 (1972).
Clinical Chemistry, vol. 20, No. 1, pp. 36–40 (1974).
Clinical Chemistry, vol. 21, No. 3, pp. 381–386, pp. 392–397 (1975).
Clinical Chemistry, vol. 21, No. 7, pp. 844–849 (1975).
Clinical Chemistry, vol. 21, No. 8, pp. 1088–1092 (1975).
Clinical Chemistry, vol. 22, No. 1, pp. 92–97 (1976).
Clinical Chemistry, vol. 22, No. 4, pp. 552–554 (1976).

*Primary Examiner*—Lionel M. Shapiro

[57] ABSTRACT

Creatine kinase MB isoenzyme can be separated from a mixture of creatine kinase isoenzymes by ion exchange chromatography. Use of a mixture of cation and anion exchange resin in this method permits elution of the MB isoenzyme from the mixed resin while the other isoenzymes are wholly or partially retained. In a preferred embodiment the mixed resin is a mixture of a weakly basic anion exchange resin and a weakly acidic cation exchange resin.

8 Claims, No Drawings

METHOD FOR ISOLATING MB CREATINE KINASE

This invention relates to a method for isolating MB creatine kinase from the MM isoenzyme, and with some modification, also from the isoenzyme BB. Creatine kinase, also referred to as creatine phosphokinase in some references, will be abbreviated CK. There are three known CK isoenzymes, the MM found primarily in skeletal muscle tissue, the BB found primarily in brain tissue and MB found primarily in heart tissue. The presence of elevated levels of CK-MB in serum is an indicator of myocardial infarction.

There are several methods for separating the CK isoenzymes including electrophoreses as reported in American Journal of Cardiology 33 P. 650 (1974) and ion-exchange chromatography as reported in Clinical Chemistry 20 p. 36 (1974). Several investigators have proposed the use of a commercial anion exchange resin having diethyl aminoethyl substituents, DEAE Sephadex, for the ion-exchange chromatographic separation; Clin. Chem. Acta, 38, pp. 285–90 (1972); Clin. Chem. 21, p. 1088 (1975). Others have proposed modifications of this procedure using DEAE cellulose, Clin. Chem. 21, p. 392 (1975), DEAE glass beads, Clin. Chem. 21, p. 844 (1975) and another commercial resin, a strong anion exchanger sold as AG MP-1 by Bio-Rad Laboratories, Clin. Chem. 22, p. 92 (1976). In all of these chromatographic procedures, the first isoenzyme to be eluted is the generally predominant CK-MM. This is usually not the isoenzyme of primary interest. Thus, these methods require additional time and an additional step to isolate the CK-MB.

This invention provides a method for eluting the CK-MB as the first fraction from an ion exchange resin bed, speeding and simplifying the analysis and making CK-MB analysis more readily adaptable to automation.

In the process of this invention, the ion exchange resin used to effect the chromatographic separation of CK isoenzymes is a mixture of cation and anion exchange resins. With proper selection of the resin and the elution conditions, the first isoenzyme to be eluted from the mixed bed resin is CK-MB. The preferred mixed bed resin is a mixture of a weakly basic anion exchange resin and a weakly acidic cation exchange resin.

It should be recognized that the choice of a resin mixture and the various elution parameters such as pH, resin bed and sample size, speed of elution and the like are interrelated. In the description of the more preferred embodiments which follows, specific resins and conditions will be recited. While these parameters are preferred, the recitation is not meant to exclude other combinations of resin or resin mixtures and elution parameters from the scope of this case. Once a choice of a particular mixed bed resin is made, determination of the optimum elution parameters can be readily made by those skilled in the art.

The preferred mixed bed resin of this invention is a mixture of a DEAE substituted crosslinked dextran anion exchange resin and a cation exchange resin in which an acrylic polymer lattice is substituted with an acidic functional group. Such resins are commercially available, the anion exchange resin being sold under the name DEAE "Sephadex" A-25 and the cation exchange resin being sold under the name "Bio-Rex 70". A ratio of from 5 to 10 settled bed volumes of the cation exchange resin for each settled bed volume of the anion resin is preferred with a volume ratio of about 6:1 being more preferred.

Kits containing the resin mixtures described above, particularly kits in which the resin is prepackaged in columns, are also within the scope of this invention. In use, the mixed resins of this invention are generally immersed in a buffer. The preferred pH range for the preferred resins of this invention is from about 6.0 to about 6.4. At the lower end of this range the CK-MM and CK-BB are more readily retained by the resin. At the upper end of the pH range CK-MB is more readily eluted but some elution of CK-BB also occurs. Increased recoveries of CK-MB and CK-BB are obtained from the column as the sample size is increased.

In the best mode for practicing the invention, the mixed bed resin is prepared as follows. DEAE-Sephadex A-25 is hydrated in a buffer, preferably morpholinethylsulfonic acid adjusted to pH 6.0 for 48 hours. At the end of this period, the pH is readjusted to 6.0 with HCl. Bio-Rex 70 (100–200 mesh) is hydrated in the same buffer as pH 6.0 for the same period, after which the pH is readjusted to 6.0 with sodium hydroxide. Fine particles are removed from both resins and one settled bed volume of the Sephadex is added to six settled bed volumes of the Bio-Rex with gentle stirring. The gentle mixing is continued for 15 minutes and the pH is adjusted to 6.0. Finally, the resin bed is washed with three bed volumes of the buffer adjusted to pH 6.0. The resin is left immersed in the buffer adjusted to pH 6.0. Under these conditions the eluant used to elute CK-MB from the column is deionized water. These conditions are preferred to accommodate the separation procedure to the test pack used on the aca Automatic Clinical Analyzer sold by E. I. du Pont de Nemours and Company.

EXAMPLE I

Columns in aca test pack headers having a volume of 1.7 ml can be packed with the mixture of Bi-Rex 70 and DEAE Sephadex A-25 prepared as described above. Each test pack is adapted to receive a single sample, 0.34 ml volume, injected onto the resin column. The samples are eluted with 2.0 ml of deionized water into the reaction chamber of the pack at the rate of 1.0 ml/min.

The presence of creatine kinase in the eluant is determined by a modification of the UV enzymatic assay described by Oliver, I. T., Biochem J., 61, p. 116 (1955) and Rosalki, S. B., J. Lab. Clin. Med., 69, p. 696 (1967). The rate of formation of $NADH_2$, which absorbs at 340 nm, is proportional to the concentration of the creatine kinase.

The Oliver-Rosalki method does not differentiate between CK isoenzymes, but the efficacy of the chromatographic separation of the isoenzymes can be demonstrated as follows.

The recovery of the three CK isoenzymes can be determined by measuring their individual activity prior to and after elution through the mixed bed resin column. The source of isoenzymes used to make these determinations is human tissue. The table below presents typical isoenzyme recovery using the mixed bed resin column as previously described.

Table I (Column Elution of CK-Isoenzymes)

| CK-Isoenzyme (In Human Serum) | Activity (IU/l) w/o Column | Activity (IU/l) w Column | % Recovery |
| --- | --- | --- | --- |
| MM | 134 | 1 | <1% |
| MB | 286 | 196 | 69% |
| MM | 197 | 2 | 1% |
| BB | 785 | 361 | 46% |

EXAMPLE II

Using the same mixture of ion exchange resins and the same column size with a sample size of 0.20 ml and eluting the column with 2.0 ml deionized water at a rate of 0.5 ml/min., essentially all of the CK-MM and CK-BB are retained while only the CK-MB isoenzyme is recovered. The effect of resin pH on the performance of the mixed bed resin column under these conditions is shown in the following table:

Table II (Column Elution of CK-Isoenzymes)

| CK-Isoenzyme (In Human Serum) | Activity (IU/l) | | | |
| --- | --- | --- | --- | --- |
| | w/o Column | w Column | | |
| | | pH of Column Resin | | |
| | | 6.1 | 6.25 | 6.4 |
| MM | 107 | 0 | 2 | 84 |
| MB | 297 | 120 | 241 | 283 |
| BB | 124 | 0 | 13 | 95 |

We claim:

1. In a process for separating the isoenzymes of creatine kinase from a mixture of the isoenzymes comprising contacting the mixture with an ion exchange resin and selectively eluting the isoenzymes from the resin, the improvement comprising contacting the mixture with a mixed bed resin containing anion exchange resin and excess cation exchange resin and initially eluting MB creatine kinase isoenzyme.

2. The process of claim 1 wherein the mixed bed resin is a mixture of a weakly basic anion exchange resin and a weakly acidic cation exchange resin.

3. The process of claim 2 wherein the anion exchange resin is a diethyl aminoethyl substituted crosslinked dextran and the cation exchange resin is an acrylic polymer lattice substituted with an acidic functional group.

4. The process of claim 2 wherein the ratio of cation exchange resin to anion exchange resin is from 5:1 to 10:1.

5. The process of claim 3 wherein the ratio of cation exchange resin to anion exchange resin is about 6:1.

6. The process of claim 4 wherein the mixed bed resin is buffered to a pH of about 6.0 to about 6.4.

7. A kit for separating MB creative kinase isoenzymes consisting essentially of a mixed bed resin comprising a mixture of a diethyl aminoethyl substituted crosslinked dextran anion exchange resin and a cation exchange resin comprising an acrylic polymer lattice substituted with an acidic functional group and wherein the ratio of cation exchange resin to anion exchange resin is 5:1 to 10:1.

8. The kit of claim 7 wherein the ratio of cation exchange resin to anion exchange resin is about 6:1 and the pH of the buffer is from about 6.0 to about 6.4.

* * * * *